United States Patent [19]

Price et al.

[11] 4,426,878

[45] Jan. 24, 1984

[54] VISCOSIMETER

[75] Inventors: John G. W. Price, Dallas, Tex.; Rene Cloarec, Paris, France

[73] Assignee: Core Laboratories, Inc., Dallas, Tex.

[21] Appl. No.: 310,657

[22] Filed: Oct. 13, 1981

[51] Int. Cl.³ .......................................... G01N 11/04
[52] U.S. Cl. ................................ 73/55; 73/861.52; 73/56
[58] Field of Search ............................. 73/55, 56, 54

[56] References Cited

U.S. PATENT DOCUMENTS

| | | | |
|---|---|---|---|
| 1,529,811 | 3/1925 | Priest | 73/56 |
| 1,602,444 | 10/1926 | Naiman | 73/54 |
| 1,810,992 | 6/1931 | Von Dallwitz-Wegner | 73/55 |
| 1,918,270 | 7/1933 | Kegl et al. | 73/55 |
| 2,934,944 | 5/1960 | Eolkin | 73/55 |
| 2,948,145 | 8/1960 | Eolkin | 73/54 |
| 3,086,386 | 4/1963 | Kapff | 73/23 |
| 3,111,838 | 11/1963 | Bucalo | 73/54 |
| 3,283,565 | 11/1966 | Müller et al. | 73/55 |
| 3,286,511 | 11/1966 | Harkness | 73/55 |
| 3,492,857 | 2/1970 | Bosco et al. | 73/54 |
| 3,559,464 | 2/1971 | Foust et al. | 73/55 |
| 3,678,733 | 7/1972 | Blatter | 73/54 |
| 3,713,327 | 1/1973 | Clemens | 73/32 |
| 3,745,811 | 7/1973 | Dure et al. | 73/30 |
| 3,943,753 | 3/1976 | Simon | 73/54 |
| 4,302,965 | 12/1981 | Johnson et al. | 73/55 |

OTHER PUBLICATIONS

Publ. "Development of High-Pr. Capillary-Tube Viscometer . . . for Methane" etc. by Giddings et al., 45 J. Chem. Phys. (578-586) 7/15/66.

Primary Examiner—Daniel M. Yasich
Attorney, Agent, or Firm—Lee C. Robinson, Jr.

[57] ABSTRACT

A viscosimeter having a first cell containing mercury or other electrically conductive fluid, a second cell containing a sample of fluid of unknown viscosity, and a pair of passages interconnecting the ends of the cells to form a closed circuit. A plurality of electrodes extend into the second cell in spaced relationship with each other along the cell's axis and are connected to an electrical circuit. Upon the opening of valves in the two passages, the conductive fluid urges the sample fluid through one of the passages and flows through the other passage into sequential contact with the electrodes in the second cell. The electrical circuit detects the rate of movement of the conductive fluid past the electrodes and produces an output signal related to the viscosity of the sample.

8 Claims, 5 Drawing Figures

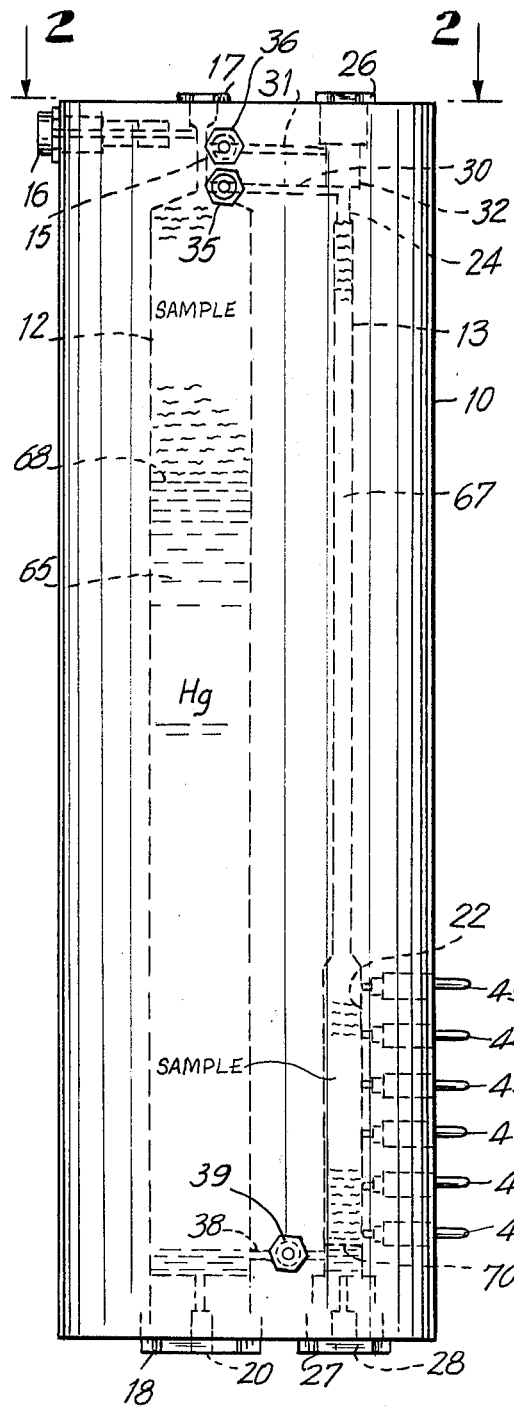

VISCOSIMETER

BACKGROUND OF THE INVENTION

This invention relates to measuring apparatus and more particularly to apparatus for measuring the viscosity of a fluid.

The present invention, while a general application, is particularly well suited for use as a viscosimeter to determine the viscosity of heavy oil or other comparatively viscous fluid at high temperatures and pressures. In the oil and gas industry, for example, accurate measurements often are needed of the viscosity of the liquid hydrocarbons found at some of the shallower depths beneath the surface of the earth, and these materials may have a viscosity as high as 10,000 centipoise. The viscosity should be measured at a temperature and pressure which at least approximate the subsurface conditions to which the material is subjected.

Heretofore, apparatus for detecting the viscosity of a fluid have exhibited a number of disadvantages. As an illustration, several types of prior apparatus for this purpose utilize a capillary tube arrangement to produce a pressure signal corresponding to the fluid viscosity, in which the surface tension of the fluid adversely affected the accuracy of the resulting measurements. In addition, and this has been of special moment in cases in which the viscosity was determined with the fluid under high pressure, the apparatus often was not sufficiently sensitive to detect small changes in the pressure signal. Viscosimeters and similar apparatus of the type previously employed frequently exhibited further difficulties in cases in which it was necessary to make blind viscosity measurements without being able to observe the fluid during the measuring operation.

SUMMARY

One general object of this invention, therefore, is to provide a new and improved viscosimeter for determining the viscosity of a fluid.

More specifically, it is an object of this invention to provide such a viscosimeter which does not depend solely on pressure measurements to ascertain the viscosity.

Another object of the invention is to provide a viscosimeter of the character indicated which is particularly well suited for determining the viscosity of the fluid with the fluid under high temperature and pressure.

A further object of this invention is to provide a viscosimeter which exhibits improved sensitivity and accuracy over a wide range of measurements.

A still further object of this invention is to provide a viscosimeter having comparatively simple mechanical and electrical components which is economical to manufacture and thoroughly reliable in operation.

In one illustrative embodiment of the invention, the viscosimeter includes a first cell containing a body of electrically conductive fluid and an elongated second cell containing a sample of fluid of unknown viscosity. A first passage and a capillary passage interconnect one pair of adjacent ends of these cells, and an additional passage interconnects the other pair of adjacent ends to form a closed circuit. Upon the opening of a valve in the additional passage, the conductive fluid flows from the first cell through the additional passage into the second cell, while the sample fluid is urged through the capillary passage and the first passage into the first cell.

In accordance with one feature of the invention, the rate of movement of the conductive fluid in the second cell is detected electrically to similarly detect the rate of movement of the sample fluid through the capillary passage. The detected rate may then be readily converted to viscosity.

In accordance with another feature of the invention, in several advantageous embodiments, a plurality of electrodes are exposed to the interior of the second cell in spaced relationship with each other along the cell's axis. Upon the opening of the valve, the conductive fluid flows into sequential contact with the electrodes to provide an extremely accurate rate of movement and hence viscosity measurement.

In accordance with a further feature of some embodiments of the invention, the specific gravity of the conductive fluid (e.g. mercury) is far in excess of that of the sample fluid. The conductive fluid serves as a gravity-operated piston to direct the sample through the capillary passage. The arrangement is such that blind viscosity measurements may be made in an extremely accurate manner with the sample under high temperature and pressure.

The foregoing and other objects, features and advantages of the invention will be more readily understood from the following description of a preferred embodiment thereof, when read with reference to the accompanying drawings.

BRIEF DESCRIPTION OF THE DRAWINGS

FIG. 1 is an elevational view of a viscosimeter in accordance with an illustrative embodiment of the invention.

FIG. 2 is a top view of the viscosimeter as seen from the line 2—2 in FIG. 1.

FIG. 5 is a schematic representation of an electrical circuit useful with the viscosimeter.

DESCRIPTION OF A PREFERRED EMBODIMENT

Referring to FIG. 1 of the drawings, the apparatus includes a cylindrical housing 10 of metal or other rigid opaque material. The housing 10 is provided with two spaced bores which define an enlarged cell 12 and a measuring cell 13. The cells 12 and 13 are of cylindrical configuration and are juxtaposed in parallel side by side relationship with each other such that the axes of the cells are located parallel to and on opposite sides of the housing axis. The diameter of the cell 12 is substantially greater than that of the cell 13 and advantageously is at least three times the diameter of this latter cell. In the illustrated embodiment, for example, the cell 12 has a diameter of one and one half inch, while the diameter of the cell 13 is one half inch.

Figure 3:
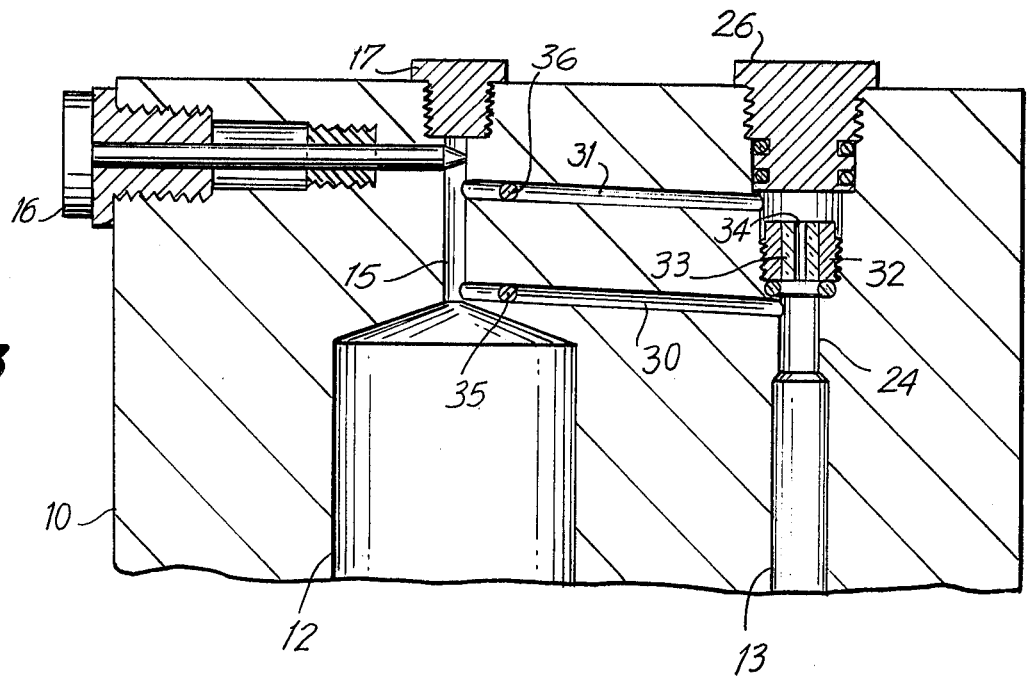
FIG. 3 is an enlarged vertical sectional view of the upper portion of the viscosimeter.
Figure 4:
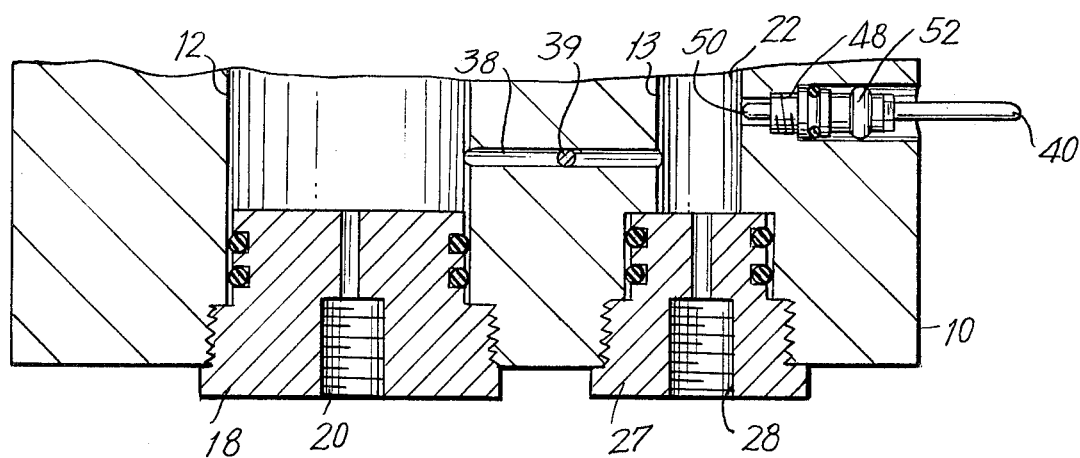
FIG. 4 is an enlarged vertical sectional view of the lower portion of the viscosimeter.

The enlarged cell 12 is provided with a reduced diameter portion 15 adjacent its upper end. As best shown in FIG. 3, a needle valve 16 extends radially into the passage formed by the portion 15 to open and close this passage. The upper end of the cell 12 above the portion 15 is sealed by a removable end cap 17, while the lower end of the cell is sealed by a removable end cap 18 (FIG. 4). This latter end cap is provided with an infeed opening 20 for purposes that will become more fully apparent hereinafter.

The diameter of the measuring cell 13 is increased over approximately the lower third of its length to provide an enlarged portion 22. A substantially shorter portion 24 of the cell 13 is located at the upper end of the cell and is of reduced diameter. The upper end of the cell is sealed by a removable end cap 26, and the lower end is sealed by a removable end cap 27. The end cap 27 includes an opening 28.

The adjacent upper ends of the enlarged cell 12 and the measuring cell 13 are interconnected by a by-pass passage 30. A second passage 31 is spaced a short distance above the passage 30 such that the axes of the two passages extend radially with respect to the housing 10. The by-pass passage 30 provides fluid communication between the lower end of the portion 15 of the cell 12 and the portion 24 of the cell 13, while the second passage 31 provides communication from a point just beneath the needle valve 16 in the portion 15 of the cell 12 to a point shortly above a threaded collar 32 in the portion 24 of the cell 13.

As best shown in FIG. 3, the collar 32 contains a glass tube 33 which defines a capillary passage 34. The passage 34 communicates with the upper end of the measuring cell 13 and is in series with the passage 31 to connect the upper end of the cell 13 with the corresponding end of the enlarged cell 12. The passage 30 also connects the upper ends of the cells 12 and 13 and is in parallel with the passages 31 and 34 to bypass these passages. The diameter of the passage 34 is substantially less than the diameters of the passages 30 and 31 and illustratively is about 0.01 to 0.02 inches.

Fluid flow through the by-pass passage 30 and the second passage 31 is controlled by respective needle valves 35 and 36. The valves 35 and 36 extend inwardly into their corresponding passages from the exterior of the housing 10 and are manually movable between open and closed positions to similarly open and close the passages.

Disposed in the lower portion of the housing 10 is an additional passage 38. The passage 38 interconnects the adjacent lower ends of the enlarged cell 12 and the measuring cell 13 and is controlled by a needle valve 39. The valve 39 extends into the passage 38 from the exterior of the housing and is movable between an open and a closed position to similarly open and close the passage. The arrangement is such that a generally rectangular closed circuit is formed from the enlarged cell 12, the passage 38, the measuring cell 13, the capillary passage 34 and the passage 31 leading back to the cell 12.

A plurality of electrodes 40–45 extend into the housing 10 and are exposed to the interior of the measuring cell 13. These electrodes are located in spaced relationship with each other along the axis of the cell 13. The electrodes 40–45 are disposed one above the other and are located in the enlarged lower portion 22 of the cell 13 with their inner ends flush with the interior wall of the cell such that the inner ends are exposed to fluid within the cell. As best shown in FIG. 4, each of these electrodes is removably positioned in a radially tapped socket 48 in the housing 10 and is provided with an electrically conductive sensing pin 50 which is exposed to the interior of the cell portion 22. A dielectric housing 52 surrounds each electrode to insulate the electrode from the housing.

As best illustrated in FIG. 5, the electrodes 40–45 are electrically connected to an electronic circuit shown schematically at 55. The circuit 55 is connected to a conventional power supply 57 and is effective to produce an output signal on a lead 58 proportional to the viscosity of the sample fluid within the viscosimeter. These values are displayed and recorded in a display unit 59.

To prepare the apparatus for a particular measurement, the valves 35, 36 and 39 are opened, and the cells 12 and 13 and the various passages are thoroughly cleaned. A body 65 of electrically conductive driving fluid is then introduced under high pressure through the infeed opening 20 in the end cap 18. Although a variety of electrically conductive driving fluids may be employed for this purpose, the electrically conductive driving fluid advantageously comprises an incompressible liquid having a specific gravity far in excess of that of the sample fluid to be measured. Mercury is preferred as a driving fluid because of its highly conductive properties and ready availability. To insure that the mercury completely fills not only the cells 12 and 13 but also the various passages, a suitable vacuum pump (not shown) may be employed to maintain suction within the apparatus.

The heavy oil or other fluid of unknown viscosity to be measured is stored under high pressure which illustratively is of the order of 5,000 pounds per square inch. This fluid is connected to the apparatus at the location of the end cap 17, and after purging the connecting line the valve 16 is opened and a sample 67 of the fluid of unknown viscosity is introduced into the cell 13. During the introduction of the sample, the mercury pressure is maintained at the infeed opening 20, and the excess mercury is withdrawn through the opening 28 in the end cap 27. The incoming sample passes through the passages 30 and 31 to substantially fill the cell 13, and it also flows into the upper portion of the cell 12.

When the mercury level in the enlarged cell 12 reaches that indicated by the dotted line 68, the valve 39 is closed to block the passage 38. The incoming sample fluid in the measuring cell 13 continues to discharge mercury from the cell 13 until the mercury level is below the lowermost electrode 40. The valve 16 is then closed to shut off the supply of sample fluid, the opening 28 is blocked to prevent the further discharge of mercury, and the by-pass valve 35 is closed to block the passage 30.

With both the body 65 of mercury and the sample 67 in place, the major portion of the enlarged cell 12 is filled with mercury to the level 68. The remainder of the cell 12 and all but the very lowest portion of the measuring cell 13 is filled with sample such that the mercury level 70 in the cell 13 is below the lowermost electrode 40. To achieve this disposition of mercury and sample, the valve 39 may be momentarily cracked open to admit a small quantity of mercury into the cell 13 below the lowermost electrode. The apparatus is rocked or pivoted to make sure the sample and mercury are in equilibrium, and it is then placed in a stable vertical position and heated to bring the sample to the desired measuring temperature, illustratively 350° F. The pressure on the sample during the measurement is maintained at the high value discussed heretofore by the addition or removal of mercury from the cell as needed.

To initiate a viscosity measurement, the valve 39 is moved to its open position to permit fluid flow through the passage 38. The mercury 65 within the cell 12 flows through the passage 38 and acts as a liquid piston to force the sample 67 upwardly within the cell 13 and through the capillary passage 34 (FIG. 3) and the passage 31 into the cell 12, thereby lowering the mercury level 68 within the cell 12 and raising the mercury level 70 within the cell 13.

As the mercury level 70 within the cell 13 reaches the lowermost electrode 40, a circuit is closed to initiate operation of a timer within the electronic circuit 55 (FIG. 5). The level 70 proceeds upwardly past the successive electrodes 41, 42 and 43 to detect the rate of movement of the mercury past the electrodes, and hence the rate of flow of the sample fluid through the capillary passage 34, and to also enable the calculation of the difference in mercury head between the two cells 12 and 13 at the time the mercury reaches the electrode 40. As the mercury continues to rise within the cell 13 and passes the electrodes 44 and 45, the resulting signals are used to cross-check the data obtained from the lower electrodes.

In accordance with Poiseuille's equation, the volume of liquid Q flowing per second through a capillary passage of length L and radius R under a pressure drop $\Delta P$ across the capillary length L is related to the viscosity of the liquid $\eta$ as follows:

$$Q = \frac{\pi \Delta P R^4}{8 L \eta}$$

The dimensions of the capillary passage 34 are in the electronic circuit 55. As the mercury or other electrically conductive fluid flows into sequential contact with the electrodes in the cell 13, the circuit 55 detects the rate of flow Q of the sample liquid through the capillary passage 34 as well as the pressure $\Delta P$. The circuit 55 produces an output signal on the lead 58 related to the viscosity $\eta$ of the sample. The thus measured viscosity data is displayed and recorded by the display 59.

In the illustrated embodiment of the invention the viscosity measurements are performed blind, that is, without the necessity for observing the heads of mercury within the cells 12 and 13. In other embodiments, particularly in cases in which the apparatus is readily accessible and the measuring temperatures and pressures are such as to permit the use of a transparent material for the housing 10, the difference in the mercury heads may be observed visually to provide a direct reading of the fluid pressure. In these latter embodiments as few as two electrodes may be employed within the cell 13 in order to detect the rate of movement of the mercury and hence of the sample fluid through the capillary passage.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A viscosimeter for determining the viscosity of a fluid sample, the viscosimeter comprising, in combination:
   a first cell containing a body of electrically conductive incompressible fluid;
   an elongated second cell containing a fluid sample, the second cell having an axis in juxtaposition with the first cell, the fluid sample having a significantly smaller specific gravity than said conductive fluid;
   a capillary passage interconnecting the first cell and one end of the second cell;
   an additional passage interconnecting the first cell and the other end of the second cell, to form a closed circuit comprising said first and second cells and said passages;
   valve means disposed in said additional passage;
   sensing means including a plurality of electrodes extending into the second cell in axial spaced relationship with each other along said second cell, the opening of said valve means permitting flow of said electrically conductive fluid from said first cell through said additional passage and into sequential contact with the electrodes in said second cell, and permitting flow of said fluid sample from said second cell through said capillary passage into said first cell; and
   circuit means electrically connected to said electrodes for detecting the rate of movement of a top surface of the conductive fluid past said electrodes and for producing an output signal representing the viscosity of the sample.

2. A viscosimeter for determining the viscosity of a fluid sample, the viscosimeter comprising, in combination:
   a first elongated cell containing a body of electrically conductive fluid;
   a second elongated cell in spaced parallel relationship with the first elongated cell and containing a fluid sample, the conductive fluid having a significantly higher specific gravity than said sample;
   a capillary passage interconnecting an upper end of the first cell and an upper end of the second cell;
   an additional passage interconnecting the other, lower end of the first cell and the other, lower end of the second cell, to form a closed circuit comprising said first and second cells and said passages;
   valve means disposed in said additional passage;
   electrode means extending into the second cell, the opening of said valve means permitting flow of said electrically conductive fluid from said first cell through said additional passage and into contact with the electrode means in said second cell, with the flow of the denser electrically conductive fluid driving a flow of said fluid sample from said second cell through said capillary passage into said first cell; and
   circuit means electrically connected to said electrode means for detecting the rate of movement of the conductive fluid past said electrode means and for producing an output signal representing the viscosity of the fluid sample.

3. A viscosimeter for determining the viscosity of a fluid sample, the viscosimeter comprising, in combination:
   a first cylindrical cell containing a body of electrically conductive incompressible fluid;
   a second cylindrical cell in spaced parallel relationship with the first cylindrical cell and containing a fluid sample, the electrically conductive incompressible fluid having a significantly higher specific gravity than said fluid sample;
   a capillary passage interconnecting an upper end of the first cell and an upper end of the second cell;
   an additional passage interconnecting the other, lower end of the first cell and the other, lower end of the second cell, to form a closed circuit comprising said first and second cells and said passages;

valve means disposed in said additional passage;

means including a plurality of electrodes extending into the second cell in spaced axial relationship with each other along said second cell, the opening of said second valve means permitting flow of said electrically conductive fluid from said first cell through said additional passage and into sequential contact with the electrodes in said second cell, and the flow of the denser electrically conductive fluid driving a flow of said fluid sample from said second cell through said capillary passage into said first cell; and circuit means electrically connected to said electrodes for detecting the rate of movement of the conductive fluid past said electrodes and for producing an output signal representing the viscosity of the sample.

4. A viscosimeter for determining the viscosity of a fluid sample, the viscosimeter comprising, in combination:

a first cylindrical cell containing a body of electrically conductive fluid;

a second cylindrical cell in spaced parallel relationship with the first cylindrical cell and containing a fluid sample;

a capillary passage interconnecting an upper end of the first cell and an upper end of the second cell and a by-pass passage interconnecting said one ends and parallel to said capillary passage;

an additional passage interconnecting the other, lower end of the first cell and the other, lower end of the second cell;

an infeed passage coupled to the upper end of the first cell for supplying the latter with said fluid sample;

first, second, third, and fourth valve means respectively disposed in said capillary passage, said additional passage, said by-pass passage, and said infeed passage;

means including a plurality of electrodes extending into the second cell in spaced relationship with each other along the axis of said second cell, the opening of said first and second valve means permitting flow of said electrically conductive fluid from said first cell through said additional passage and into sequential contact with the electrodes in said second cell, and permitting flow of said fluid sample from said second cell through said capillary passage into said first cell; and circuit means electrically connected to said electrodes for detecting the rate of movement of the conductive fluid past said electrodes and for producing an output signal representing the viscosity of the sample.

5. A viscosimeter as defined in claim 4, in which at least four electrodes extend into the second cell in axially spaced relationship with each other along said second cell.

6. A viscosimeter for determining the viscosity of a fluid sample, wherein the fluid sample is tested for viscosity under conditions of elevated pressures at which gasses dissolved in the fluid sample may alter its viscosity, comprising a housing capable of sustaining pressures on the order of 5,000 psig and provided with a first elongated cell and a measuring cell disposed in parallel, side by side relationship, and having a capillary passage joining the upper ends of the first elongated cell and the measuring cell and an additional passage joining the lower ends of these cells, such that the measuring cell, the capillary passage, the first, elongated cell, and the additional passage form a closed loop;

a valve disposed in said closed loop for selectively closing and opening said loop to permit passage of fluid through said capillary tube;

a body of driving fluid of high specific gravity relative to said fluid sample and immiscible therewith disposed in said first cell and defining a pressure head between a surface of the driving fluid in said first cell and a surface thereof in said measuring cell; with said fluid sample being contained in said closed loop above the surface therein of the driving fluid, and with said body of driving fluid being operative as a fluid piston, when said valve is open, to urge said fluid sample through said capillary passage at a pressure differential determined by said pressure head;

a plurality of sensing means disposed at axially spaced intervals in said measuring cell to sense the passage upwards of the surface therein of said driving fluid sequentially therepast; and circuit means electrically connected to said sensing means for detecting the rate of movement of the surface of said driving fluid past said sensing means and for producing an output signal representing the viscosity of the fluid sample.

7. A viscosimeter according to claim 6, wherein said driving fluid is mercury, and said pressure head is on the order of several centimeters of mercury.

8. A viscosimeter according to claim 6, wherein said circuit means provides said output signal in accordance with Poiseuille's equation $$m = \frac{\pi \Delta P R^4}{8LQ}$$

where
  m is the viscosity of the fluid sample;
  $\Delta P$ is the pressure head;
  R is the radius of the capillary passage;
  L is the length of the capillary passage; and
  Q is the rate of flow of said fluid sample through said capillary passage.

* * * * *